United States Patent
Richter et al.

(10) Patent No.: US 7,807,710 B2
(45) Date of Patent: Oct. 5, 2010

(54) MACROCYCLES FOR THE TREATMENT OF CANCER

(75) Inventors: Wolfgang Richter, Munich (DE); Bernd Henkel, Eppstein-Bremthal (DE); Michael W. Cappi, Munich (DE)

(73) Assignee: R&D-Biopharmaceuticals GmbH, Martinsried (DE)

( * ) Notice: Subject to any disclaimer, the term of this patent is extended or adjusted under 35 U.S.C. 154(b) by 540 days.

(21) Appl. No.: 10/573,365

(22) PCT Filed: Sep. 27, 2004

(86) PCT No.: PCT/EP2004/010820

§ 371 (c)(1), (2), (4) Date: Mar. 5, 2007

(87) PCT Pub. No.: WO2005/030767

PCT Pub. Date: Apr. 7, 2005

(65) Prior Publication Data

US 2007/0225265 A1    Sep. 27, 2007

(30) Foreign Application Priority Data

Sep. 26, 2003 (DE) ................ 103 44 882

(51) Int. Cl.
A61K 31/357    (2006.01)
C07D 321/12    (2006.01)

(52) U.S. Cl. ...................... 514/450; 549/274
(58) Field of Classification Search .......... 549/274
See application file for complete search history.

(56) References Cited

U.S. PATENT DOCUMENTS

2004/0082651 A1    4/2004  Wessjohann et al.

FOREIGN PATENT DOCUMENTS

| WO | WO-93/10121 A | 5/1993 |
|----|---------------|--------|
| WO | WO-99/02514 A | 1/1999 |
| WO | WO 02/32844 A2 | 4/2002 |

OTHER PUBLICATIONS

Vippagunta, et al. Advanced Drug Delivery Reviews 48 (2001) pp. 3-26.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org/wiki/Cancer.*
Greene, T.W. & Wuts, P.G.M., *Protective Groups in Organic Synthesis*, Third Ed., John Wiley & Sons, New York (1999), pp. 494-648.
Mulzer et al., *C.R. Chimie*, 11: 1336-1368 (2008).
Nicolaou et al., *Angew. Chem. Intl. Ed. Engl.*, 35 (20): 2399-2401 (1996).
Smith, M. B. & March J., *March's Advanced Organic Chemistry*, Fifth Ed., John Wiley & Sons, Inc., New York (2001), pp. 499-501 and 775-777.

* cited by examiner

*Primary Examiner*—Rebecca L Anderson
*Assistant Examiner*—Shawquia Young
(74) *Attorney, Agent, or Firm*—Leydig, Voit & Mayer, Ltd

(57) ABSTRACT

The invention relates to the novel macrocycles of general formula (I) and to their use in the treatment of tumor diseases.

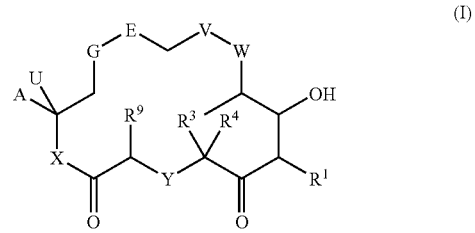

(I)

12 Claims, No Drawings

MACROCYCLES FOR THE TREATMENT OF CANCER

Epothilones (DE 4138042) are natural products with exceptional biological effects, for example as mitosis inhibitors, microtubuli-modifying agents, cytotoxics or fungicides. In particular they show paclitaxel-similar properties and still surpass Paclitaxel (Taxol™) in some tests in activity. There are currently some derivates in clinical studies for the treatment of several cancers (Nicolaou et al. Angew. Chem. Int. Ed. 1998, 37, 2014-2045; Flörsheimer et al. Expert Opin. Ther. Patents 2001, 11, 951-968).

It was objective of the present invention to provide new epothilone-like derivates which show a better profile concerning their preclinical and clinical development potential.

The present invention provides compounds of the general formula (I):

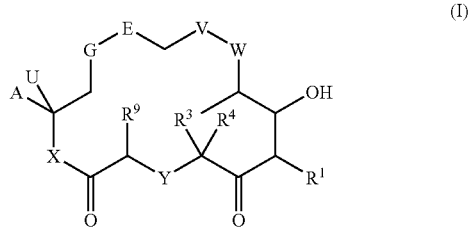

wherein

A is a heteroalkyl-, a heterocycloalkyl-, a heteroalkyl cycloalkyl-, a heteroaryl- or a heteroarylalkyl group, U is a hydrogen atom, a heteroalkyl-, a heterocycloalkyl-, a heteroalkylcycloalkyl-, a heteroaryl- or a heteroarylalkyl group, G-E is selected from the following groups,

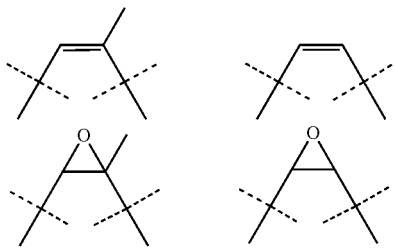

or is part of an optionally substituted phenyl ring,

V—W is a group of the formula CH—CH or C=C (cis or trans), $R^1$ is a $C_1$-$C_4$ alkyl- or a $C_3$-$C_4$-Cycloalkyl group, X is oxygen or a group of the formula $NR^2$, wherein $R^2$ is hydrogen, an alkyl-, alkenyl-, alkynyl-, heteroalkyl-, aryl-, heteroaryl-, cycloalkyl-, alkylcycloalkyl-, heteroalkylcycloalkyl-, heterocycloalkyl-, aralkyl- or a heteroaralkylrest, Y is oxygen or a group of the formula $NR^{10}$, wherein $R^{10}$ is a hydrogen atom, an oxygen atom (N-oxide), a OH, $NH_2$, alkyl- or a heteroalkyl group (as for example an alkyloxy-, alkylamino- or dialkylamino group).

$R^3$ and $R^4$ are independent of each other a hydrogen atom, a $C_1$-$C_4$-alkyl group or together part of a cycloalkyl group with 3 or 4 ring atoms, R9 is a hydrogen atom, a alkyl-, alkenyl-, alkynyl-, heteroalkyl-, aryl-, heteroaryl-, cycloalkyl-, alkylcycloalkyl-, heteroalkylcycloalkyl-, heterocycloalkyl-, aralkyl- or a heteroaralkyl group, or a pharmacologically acceptable salt, solvate, hydrate or a pharmacologically acceptable formulation of the same ones.

The term alkyl refers to a saturated, straight or branched chain alkyl group, containing from 1 to 20 carbon atoms, preferably from 1 to 12 carbon atoms, more preferably containing 1 to 6 carbon atoms, for example the methyl-, ethyl-, isopropyl-, isobutyl-, tert-butyl, n-hexyl-, 2,2-dimethylbutyl- or n-octyl group.

The terms alkenyl and alkynyl refer at least in part to unsaturated, straight or branched chain alkyl groups that containing from 2 to 20 carbon atoms, preferably from 2 to 12 carbon atoms, more preferably containing from 2 to 6 carbon atoms, for example the allyl-, acetylenyl-, propargyl-, isoprenyl- or hex-2-enyl-group.

The term heteroalkyl refers to a alkyl-, a alkenyl- or a alkynyl group, wherein one or more (preferably 1, 2 or 3) carbon atoms are replaced by an oxygen-, nitrogen-, phosphorus, boron or sulphur atom (preferably oxygen, sulphur or nitrogen), for example an alkyloxy group, as for example methoxy or ethoxy, or a methoxymethyl-, nitrile-, methylcarboxyalkylester- or 2,3-dioxyethyl-group. The term heteroalkyl refers furthermore to a carboxylic acid or a group derived from a carboxylic acid as for example acyl, acyloxy, carboxyalkyl, carboxyalkylester, such as for example methylcarboxyalkylester, carboxyalkylamide, alkoxycarbonyl or alkoxycarbonyloxy.

The term cycloalkyl or, respectively cyclo- refers to a satisfied or partially unsaturated cyclic group, having one or more rings, formed by 3 to 14 carbon atoms, preferably 3 to 10 carbon atoms, for example the cyclopropyl-, cyclohexyl-, tetralin- or cyclohex-2-enyl-group.

The term heterocycloalkyl or, respectively heterocyclo-, refers to a cycloalkyl group as defined above, wherein one or more (preferably 1, 2 or 3) carbon atoms are replaced by an oxygen-, nitrogen, phosphorus or sulphur atom, such as for example the piperidine-, morpholine-, tetrahydrofuran-, tetrahydrothiophen-, N-methylpiperazine or N-phenylpiperazine group.

The terms alkylcycloalkyl or, respectively heteroalkyl-cycloalkyl, refer to groups, that according to the above definitions contain both cycloalkyl- or, respectively heterocycloalkyl, as well as alkyl-, alkenyl-, alkynyl- and/or heteroalkyl groups.

The term aryl or, respectively Ar refers to an aromatic group that has one or more rings, formed by 5 to 14 carbon atoms, preferably 5 or 6 to 10 carbon atoms, for example a phenyl-, naphthyl-, 2-, 3- or 4-methoxyphenyl-, 2-, 3- or 4-ethoxyphenyl-, 4-carboxyphenylalkyl- or 4-hydroxyphenyl group.

The term heteroaryl refers to an aryl group, wherein one or more (preferably 1, 2 or 3) carbon atoms are replaced by an oxygen-, nitrogen, phosphorus or sulphur atom, such as for example 4-pyridyl-, 2-imidazolyl-, 3-pyrazolyl-, oxazolyl-, thiazolyl-, thiophene and isochinolinyl group.

The terms aralkyl or, respectively heteroaralkyl refer to groups, that according to the above definitions comprise of both aryl- or, respectively heteroaryl- as well as alkyl-, alkenyl-, alkynyl- and/or heteroalkyl- and/or cycloalkyl- and/or heterocycloalkyl groups, for example the tetrahydroisochinolinyl-, benzyl, 2- or 3-ethyl-indolyl- or 4-methylpyridino group.

The terms alkyl, alkenyl, alkinyl, heteroalkyl, cycloalkyl, heterocycloalkyl, aryl, heteroaryl, aralkyl and heteroaralkyl as well as "optionally substituted" refer also to groups, in which one or more hydrogen atoms of such groups are replaced through fluorine, chlorine, bromine or iodine atoms or through OH, SH, $NH_2$ or $NO_2$ groups. These terms refer additionally to groups, which are substituted with unsubstituted alkyl-, alkenyl-, alkynyl-, heteroalkyl-, cycloalkyl-, heterocycloalkyl-, aryl-, heteroaryl-, aralkyl- or heteroaralkyl groups as defined herein.

Compounds of the formula (I) can contain one or more chirality centers due to their substitution pattern. The present invention comprises of therefore both all pure enantiomers and all pure diastereoisomers, as well as also their mixtures in every possible ratio of the mixtures. Furthermore, the present invention also comprises of all cis/trans-isomers of the compounds of the general formula (I) as well as their mixtures.

Preferred are compounds of the formula (I), wherein A is a group of the formula is —C($CH_3$)=$CHR^5$ or —CH=$CHR^5$, wherein $R^5$ is a heteroaryl- or a heteroarylalkyl group.

Further preferred are compounds of the formula (I), wherein A is a group of the general formula (II) or (III):

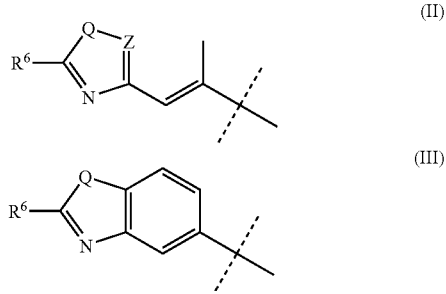

wherein Q sulphur, oxygen or a group of the formula $NR^7$ wherein $R^7$ is hydrogen, a $C_1$-$C_4$ alkyl group or a $C_1$-$C_4$-heteroalkyl group, z is nitrogen or a CH group and $R^6$ is a group of the formula $OR^8$ or $NHR^8$, a alkyl-, alkenyl, alkynyl- or a heteroalkyl group (preferably a group of the formula $CH_2OR^8$ or $CH_2NHR^8$), wherein $R^8$ is a hydrogen, a $C_1$-$C_4$ alkyl group or a $C_1$-$C_4$-heteroalkyl group (preferably a hydrogen atom).

Z is especially preferred a CH group.

Moreover preferred are compounds of the formula (I) wherein Q is sulphur or oxygen.

Further preferred are compounds of the formula (I), wherein $R^6$ is a group of the formula $CH_3$, $CH_2OH$ or $CH_2NH_2$.

Further preferred are compounds of the formula (I), wherein U is hydrogen, a $CF_3$ or a methyl group (especially preferred a hydrogen atom).

Further preferred $R^2$ is a hydrogen atom or a $C_1$-$C_4$ alkyl group (especially preferred a hydrogen atom).

Furthermore preferred are compounds of the formula (I), wherein X is oxygen.

Additionally preferred $R^1$ is a methyl, ethyl- or propyl group; especially preferred a methyl group.

Further preferred $R^3$ and $R^4$ are methyl groups.

Further preferred $R^9$ is the side chain of a natural amino acid; in particular a hydrogen atom.

Furthermore preferred Y is oxygen or a group of the formula NH, NOH or NO.

Examples of pharmacologically acceptable salts of compounds of the formula (I) are salts (or mixed salt) of physiologically acceptable mineral acids such as hydrochloric acid, sulphuric acid and phosphoric acid or salts of organic acids such as methanesulphonic acid, p-toluenesulfonic acid, lactic acid, acetic acid, trifluoroacetic acid, citric acid, succinic acid, fumaric acid, maleic acid and salicylic acid. Compounds of the formula (I) may be solvated, especially hydrated. The hydratisation can occur for example during the process of production or as a consequence of the hygroscopic nature of the initially anhydrous compounds of the formula (I). If the compounds of the Formula (I) contain asymmetric C-atoms, they may be present either as achiral compounds, diastereoisomer-mixtures, mixtures of enantiomers or as optically pure compounds. Furthermore, the present invention relates also to all cis/trans-isomers of the present compounds of the general Formula (I) as well as their mixtures.

The pharmaceutical compositions according to the present invention contain at least a compound of the formula (I) as active agent and optionally carriers and/or adjuvants.

The present invention also relates to pro-drugs (for a definition and examples see R. B. Silverman, Medical Chemistry, VCH Weinheim, 1995, chapter 8, p. 361ff), which are composed of a compound of the Formula (I) and at least one pharmacologically acceptable protective group which will be cleaved off under physiological conditions, for example a alkoxy, aralkyloxy, acyl or acyloxy group, such as ethoxy-, benzyloxy-, acetyl or acetyloxy group.

Except for the already described cancer diseases the compounds of the present invention are of great interest for the treatment of further diseases such as autoimmune diseases, inflammatory diseases, tumor diseases and other diseases which are to connected to failure of cell growths.

The present invention also relates to the therapeutic use of the compounds of the Formula (I), their pharmacologically acceptable salts and/or solvates and hydrates as well as their formulations and pharmaceutical compositions.

Also the use of these active agents for the production of drugs for the treatment of cancer diseases is object of the present invention. In general, compounds of the Formula (I) will be administered by using the known and acceptable modes known in the art, either separately or in combination with any other therapeutic agent. Such therapeutically useful agents can be administered by one of the following routes: oral, e.g. as dragees, coated tablets, pills, semisolids, soft or hard capsules, solutions, emulsions or suspensions; parenteral, for example as injectable solution; rectal as suppositories; by inhalation, for example as powder formulation or spray, transdermal or intranasal. For the production of such tablets, pills, semisolids, coated tablets, dragees and hard gelatin capsules the therapeutically useful product may be mixed with pharmaceutically inert, inorganic or organic excipients, as are for example lactose, sucrose, glucose, gelatin, malt, silica gel, starch or derivates thereof, talc, stearic acid or their salts, dry skim milk and the like. For the production of soft capsules one may use excipients as are for example vegetable oils, petroleum, animal or synthetic oils, wax, fat, polyols. For the production of liquid solutions and syrups one may use excipients as for example water, alcohols, aqueous saline, aqueous dextrose, polyols, glycerin, vegetable oils, petroleum, animal or synthetic oils. For suppositories one may use excipients as for example vegetable oils, petroleum, animal or synthetic oils, wax, fat and polyols. For aerosol formulations one may use compressed gases suitable for this purpose as for example oxygen, nitrogen, rare gases and carbon dioxide. The pharmaceutically useful agents may also contained additives for conservation, stabilization, emulsifiers, sweeteners, flavors, salts for the change of the osmotic pressure, buffers, coating additives and antioxidants.

Combinations with other therapeutic agents may include other therapeutically useful agents which usually are used for the treatment of cancer diseases.

For the treatment of cancer diseases the dose of the biologically active compound related to this invention can vary within wide borders and can be adjusted to the individual needs. In general, a dose of 1 μg to 100 mg/kg body weight per day is appropriate, with a preferred dose of 10 μg to 25 mg/kg per day. In appropriate cases the dose may be also lower or higher than the values given above.

EXAMPLES

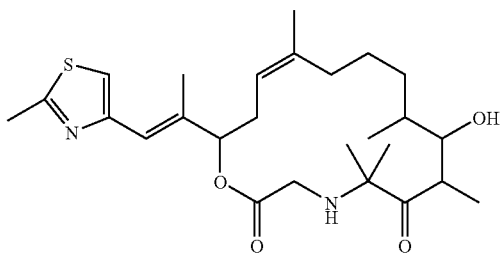

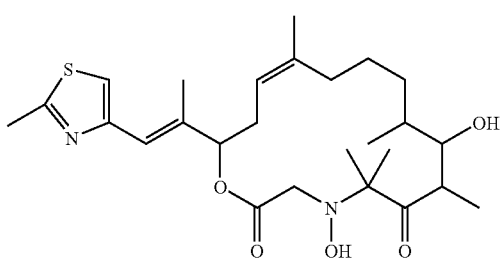

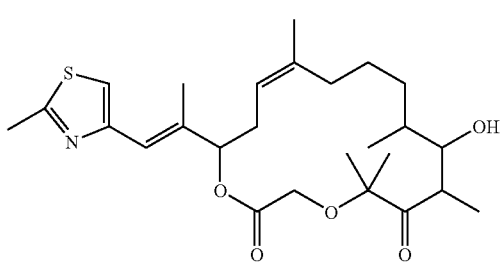

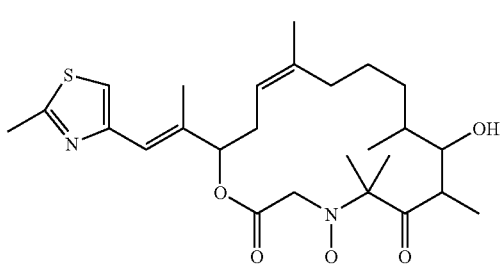

The invention claimed is:
1. A compound of the formula (I):

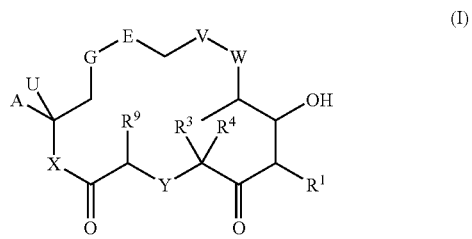

(I)

wherein

A is a heteroalkyl-, heterocycloalkyl-, heteroalkyl-cycloalkyl-, heteroaryl- or heteroarylalkyl group, U is hydrogen, a heteroalkyl-, heterocycloalkyl-, heteroalkylcycloalkyl-, heteroaryl- or heteroaryl-alkyl group, G-E is selected from the following groups,

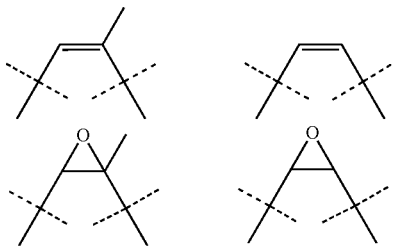

V—W is a group of the formula CH—CH or C=C (cis or trans), $R^1$ is a $C_1$-$C_4$ alkyl- or a $C_3$-$C_4$-cycloalkyl group, X is oxygen, Y is oxygen, $R^3$ and $R^4$ are independently of each other hydrogen, a $C_1$-$C_4$ alkyl group or together are part of a cycloalkyl group with 3 or 4 ring atoms, and $R^9$ is hydrogen, a alkyl-, alkenyl-, alkynyl-, heteroalkyl-, aryl-, heteroaryl-, cycloalkyl-, alkyl-cycloalkyl-, heteroalkylcycloalkyl-, heterocyclo-alkyl-, aralkyl- or a heteroaralkyl group or a pharmacologically acceptable salt thereof.

2. A compound of claim 1 wherein A is a group of the formula —C(CH$_3$)=CHR$^5$ or —CH=CHR$^5$, wherein R$^5$ is a heteroaryl- or a heteroarylalkyl group.

3. A compound of claim 1 wherein A is a group of the formula (II) or (III):

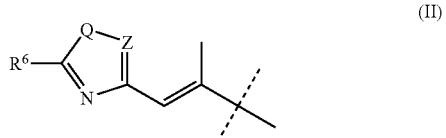

(II)

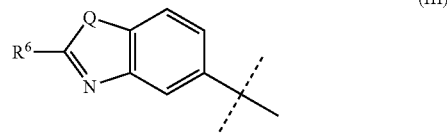

(III)

wherein

Q is sulphur, oxygen or a group of the formula $NR^7$ wherein $R^7$ is hydrogen, a $C_1$-$C_4$ alkyl group or a $C_1$-$C_4$-heteroalkyl group, Z is nitrogen or a CH group and $R^6$ is a group of the formula $OR^8$ or $NHR^8$, a alkyl-, alkenyl, alkynyl- or a heteroalkyl group, wherein $R^8$ is hydrogen, a $C_1$-$C_4$-alkyl group or a $C_1$-$C_4$-heteroalkyl group.

4. A compound of claim 3 wherein Z is a CH-group.

5. A compound of claim 3 wherein Q is sulphur or oxygen.

6. A compound of claim 3 wherein $R^6$ is a group of the formula $CH_3$, $CH_2OH$ or $CH_2NH_2$.

7. A compound of claim 1 wherein $R^1$ is a methyl group.

8. A compound of claim 1 wherein $R^3$ and $R^4$ are methyl groups.

9. A compound of claim 1 wherein U is hydrogen.

10. A compound of claim 1 wherein $R^9$ is hydrogen.

11. A pharmaceutical composition comprising a compound of claim 1.

12. The pharmaceutical composition of claim 11 further comprising one or more carriers and/or adjuvants.

* * * * *